(12) United States Patent
Boulain et al.

(10) Patent No.: US 9,540,670 B2
(45) Date of Patent: Jan. 10, 2017

(54) MUTATED T7 RNA POLYMERASES

(71) Applicants: bioMérieux, Marcy-l'Etoile (FR);
Commissariat à l'Energie Atomique et Aux Energies Alternatives, Paris (FR)

(72) Inventors: Jean-Claude Boulain, Villebon sur Yvette (FR); Janie Dassa, Palaiseau (FR); Frédéric Ducancel, Longjumeau (FR); Bruno H. Muller, Antony (FR); Alain Troesch, Genas (FR); Laurent Mesta, Genas (FR)

(73) Assignees: bioMérieux, Marcy l'Etoile (FR); Commissariat à l'Energie Atomique et Aux Energies Alternatives, Paris (FR)

( * ) Notice: Subject to any disclaimer, the term of this patent is extended or adjusted under 35 U.S.C. 154(b) by 199 days.

(21) Appl. No.: 14/349,976

(22) PCT Filed: Oct. 8, 2012

(86) PCT No.: PCT/EP2012/069886
§ 371 (c)(1),
(2) Date: Sep. 25, 2014

(87) PCT Pub. No.: WO2013/050609
PCT Pub. Date: Apr. 11, 2013

(65) Prior Publication Data
US 2015/0024435 A1    Jan. 22, 2015

(30) Foreign Application Priority Data

Oct. 6, 2011 (FR) ..................... 11 59051

(51) Int. Cl.
*C12N 9/12*    (2006.01)
*C12P 19/34*    (2006.01)

(52) U.S. Cl.
CPC ............. *C12P 19/34* (2013.01); *C12N 9/1247* (2013.01); *C12Y 207/07006* (2013.01)

(58) Field of Classification Search
None
See application file for complete search history.

(56) References Cited

U.S. PATENT DOCUMENTS

| 4,952,496 A | 8/1990 | Studier et al. |
| 5,385,834 A | 1/1995 | Ikeda |

FOREIGN PATENT DOCUMENTS

| EP | 0329822 A2 | 8/1989 |
| EP | 0373960 A2 | 6/1990 |
| EP | 0408295 A2 | 1/1991 |
| EP | 0682121 A1 | 11/1995 |
| EP | 1137781 A1 | 10/2001 |
| EP | 1261696 A1 | 12/2002 |
| JP | 2009213497 A | 9/2009 |
| JP | 2009213499 A | 9/2009 |
| WO | WO-8810315 A1 | 12/1988 |
| WO | WO-8901050 A1 | 2/1989 |
| WO | WO-9105866 A1 | 5/1991 |
| WO | WO-2010016621 A1 | 2/2010 |

OTHER PUBLICATIONS

Ngo et al. in The Protein Folding Problem and Tertiary Structure Prediction, 1994, Merz et al. (ed.), Birkhauser, Boston, MA, pp. 433 and 492-495.*
Thermo Scientific, "Zeba™ Spin Desalting Columns, 7K MWCO", 2013, 2 pages.
Stratagene; "QuickChange™ Site-Directed Mutagenesis Kit"; Instruction Manual, Catalog #200518, Revision #108005h; 1998; 19 pages.
Barton, Kenneth, A., et al., "Regeneration of Intact Tobacco Plants Containing Full Length Copies of Genetically Engineered T-DNA, and Transmission of T-DNA to R1 Progeny", Cell, vol. 32, Apr. 1983, pp. 1033-1043.
Arnaud, Nadege, et al., "Construction and expresson of a modular gene encoding bacteriophage T7 RNA polymerase", Elsevier, Gene 199, 1997, pp. 149-156.
Beckert, Bertrand, et al., "Synthesis of RNA by in Vitro Transcription", Methods in Molecular Biology 703, 2011, pp. 29-41.
Bradford, Marion, M., "A Rapid and Sensitive Method for the Quantitation of Microgram Quantities of Protein Utilizing the Principle of Protein-Dye Binding", Analytical Biochemistry 72, 1976, pp. 248-254.
Compton, J., "Nucleic acid sequence-based amplification", Nature, vol. 350, Mar. 7, 1991, pp. 91-92.
Daniel, R.M., "The upper limits of enzyme thermal stability", Enzyme and Microbial Technology, vol. 19, 1996, pp. 74-79.
Deiman, Birgit, et al., "Characteristics and Applications of Nucleic Acid Sequence-Based Amplification (NASBA)", Molecular Biotechnology, vol. 20, 2002, pp. 163-179.
Eijsink, Vincent G.H., et al., "Directed evolution of enzyme stability", Biomolecular Engineering, vol. 22, 2005, pp. 21-30.
Gill, Pooria, et al., "Nucleic Acid Isothermal Amplification Technologies—A Review", Nucleosides, Nucleotides, and Nucleic Acids, vol. 27, 2008, pp. 224-243.
Hirano, Nobutaka, et al., "Enhancement of the Enzymatic Activity of Ribonuclease HI from *Thermus thermophilus* HB8 with a Suppressor Mutation Method", Biochemistry, vol. 39, 2000, pp. 13285-13294.
Ikeda, Richard, A., et al., "T7 promoter contacts essential for promoter activity in vivo", Nucleic Acids Research, vol. 20, No. 10, 1992, pp. 2517-2524.
Ikeda, Richard, A., et al., "In Vivo and in Vitro Activities of Point Mutants of the Bacteriophage T7 RNA Polymerase Promoter", Biochemistry, 31, 1992, pp. 9073-9080.
Kotsuka, Takashi, et al., "Further Stabilization of 3-Isopropylmalate Dehydrogenase of an Extreme Thermophile, *Thermus thermophilus*, by a Suppressor Mutation Method", Journal of Bacteriology, vol. 178, No. 3, Feb. 1996, pp. 723-727.

(Continued)

*Primary Examiner* — Richard Hutson
(74) *Attorney, Agent, or Firm* — Winstead PC (57) ABSTRACT

The present invention pertains to a mutated T7 RNA polymerase and its use, the T7 RNA polymerase being mutated at position 744, the glutamine (Q) being replaced by an amino acid selected from arginine (Q744R), leucine (Q744L) or proline (Q744P).

12 Claims, 4 Drawing Sheets

(56) References Cited

OTHER PUBLICATIONS

Lee, Bokhui, et al., "Efficient Colorimetric Assay of RNA Polymerase Activity Using Inorganic Pyrophosphatase and Ammonium Molybdate", Bull. Korean Chem Soc., vol. 30, No. 10, 2009, pp. 2485-2488.

Lenstra, J.A., et al, "Mapping of viral epitopes with prokaryotic expression products", Arch Virol, 110, 1990, pp. 1-24.

Liu, Jianwei, et el., "Real-Time Monitoring in Vitro Transcription Using Molecular Beacons", Analytical Biochemistry 300, 2002, pp. 40-45.

Luckow, Verne, A., et al., "Trends in the Development of Baculovirus Expression Vectors", Bio/technology, vol. 6, Jan. 1988, pp. 47-55.

Lukavsky, Peter, J., et al., "Large-scale preparation and purification of polyacrylamide-free RNA oligonucleotides", RNA Society, vol. 10, No. 5, 2004, pp. 889-893.

Martin, Craig, T., et al., "Kinetic Analysis of T7 RNA Polymerase-Promoter Interactions with Small Synthetic Promoters", Biochemistry, 26, 1987, pp. 2690-2696.

Martin, Craig, T., et al, "Processivity in Early Stages of Transcription by T7 RNA Polymerase", Biochemistry, 27, 1988, pp. 3966-3974.

Nayak, Dhananjaya, et al., "Functional Architecture of T7 RNA Polymerase Transcription Complexes", J Mol Biol., 371(2), Aug. 10, 2007, 18 pages.

Sambrook, et al., "Expression of Cloned Genes in *Escherichia coli*", Molecular Cloning, A Laboratory Manuel, 1989, 44 pages.

Mead, David A., et al., "Chimeric Single-Stranded DNA Phage-Plasmid Cloning Vectors", 1988, pp. 85-100.

Ury, Alain, "International Search Report," prepared for PCT/EP2012/069886, as mailed Dec. 10, 2012, 3 pages.

Gardner, Lisa P., et al., "Initiation, Elongation, and Processivity of Carboxyl-Terminal Mutants of T7 RNA Polymerase," Biochemistry, vol. 36, No. 10, 1997, pp. 2908-2918.

\* cited by examiner

SEQUENCE LISTING

```
<160> NUMBER OF SEQ ID NOS: 16

<210> SEQ ID NO 1
<211> LENGTH: 2652
<212> TYPE: DNA
<213> ORGANISM: Bacteriophage T7

<400> SEQUENCE: 1
atgaacacga ttaacatcgc taagaacgac ttctctgaca tcgaactggc tgctatcccg     60
ttcaacactc tggctgacca ttacggtgag cgtttagctc gcgaacagtt ggcccttgag    120
catgagtctt acgagatggg tgaagcacgc ttccgcaaga tgtttgagcg tcaacttaaa    180
gctggtgagg ttgcggataa cgctgccgcc aagcctctca tcactaccct actccctaag    240
atgattgcac gcatcaacga ctggtttgag gaagtgaaag ctaagcgcgg caagcgcccg    300
acagccttcc agttcctgca agaaatcaag ccggaagcct agcgtacat caccattaag    360 accactctgg cttgcctaac cagtgctgac aatacaaccg ttcaggctgt agcaagcgca    420
```

```
atcggtcggg ccattgagga cgaggctcgc ttcggtcgta tccgtgacct tgaagctaag    480
cacttcaaga aaaacgttga ggaacaactc aacaagcgcg tagggcacgt ctacaagaaa    540
gcatttatgc aagttgtcga ggctgacatg ctctctaagg gtctactcgg tggcgaggcg    600
tggtcttcgt ggcataagga agactctatt catgtaggag tacgctgcat cgagatgctc    660
attgagtcaa ccggaatggt tagcttacac cgccaaaatg ctggcgtagt aggtcaagac    720
tctgagacta tcgaactcgc acctgaatac gctgaggcta tcgcaacccg tgcaggtgcg    780
ctggctggca tctctccgat gttccaacct tgcgtagttc ctcctaagcc gtggactggc    840
attactggtg gtggctattg ggctaacggt cgtcgtcctc tggcgctggt gcgtactcac    900
agtaagaaag cactgatgcg ctacgaagac gtttacatgc ctgaggtgta caaagcgatt    960
aacattgcgc aaaacaccgc atggaaaatc aacaagaaag tcctagcggt cgccaacgta   1020
atcaccaagt ggaagcattg tccggtcgag acatccctg cgattgagcg tgaagaactc    1080
ccgatgaaac cggaagacat cgacatgaat cctgaggctc tcaccgcgtg aaacgtgct    1140 gccgctgctg tgtaccgcaa ggacaaggct cgcaagtctc gccgtatcag ccttgagttc   1200
atgcttgagc aagccaataa gtttgctaac cataaggcca tctggttccc ttacaacatg   1260
gactggcgcg gtcgtgttta cgctgtgtca atgttcaacc cgcaaggtaa cgatatgacc   1320
aaaggactgc ttacgctggc gaaaggtaaa ccaatcggta aggaaggtta ctactggctg   1380
aaaatccacg gtgcaaactg tgcgggtgtc gataaggttc cgttccctga gcgcatcaag   1440
ttcattgagg aaaaccacga gaacatcatg gcttgcgcta agtctccact ggagaacact   1500
tggtgggctg agcaagattc tccgttctgc ttccttgcgt tctgctttga gtacgctggg   1560
gtacagcacc acggcctgag ctataactgc tcccttccgc tggcgtttga cgggtcttgc   1620
tctggcatcc agcacttctc cgcgatgctc cgagatgagg taggtggtcg cgcggttaac   1680
ttgcttccta gtgaaaccgt tcaggacatc tacgggattg ttgctaagaa agtcaacgag   1740
attctacaag cagacgcaat caatgggacc gataacgaag tagttaccgt gaccgatgag   1800
aacactggtg aaatctctga gaaagtcaag ctgggcacta aggcactggc tggtcaatgg   1860
ctggcttacg gtgttactcg cagtgtgact aagcgttcag tcatgacgct ggcttacggg   1920
tccaaagagt tcggcttccg tcaacaagtg ctggaagata ccattcagcc agctattgat   1980
tccggcaagg gtctgatgtt cactcagccg aatcaggctg ctggatacat ggctaagctg   2040
atttgggaat ctgtgagcgt gacggtggta gctgcggttg aagcaatgaa ctggcttaag   2100
tctgctgcta agctgctggc tgctgaggtc aaagataaga agactggaga gattcttcgc   2160
aagcgttgcg ctgtgcattg ggtaactcct gatggtttcc ctgtgtggca ggaatacaag   2220
aagcctattc agacgcgctt gaacctgatg ttcctcggtc agttccgctt acagcctacc   2280
attaacacca acaaagatag cgagattgat gcacacaaac aggagtctgg tatcgctcct   2340
aactttgtac acagccaaga cggtagccac cttcgtaaga ctgtagtgtg gcacacgag    2400 aagtacggaa tcgaatcttt tgcactgatt cacgactcct tcggtaccat tccggctgac   2460
gctgcgaacc tgttcaaagc agtgcgcgaa actatggttg acacatatga gtcttgtgat   2520
gtactggctg atttctacga ccagttcgct gaccagttgc acgagtctca attggacaaa   2580
atgccagcac ttccggctaa aggtaacttg aacctccgtg acatcttaga gtcggacttc   2640
gcgttcgcgt aa                                                      2652

<210> SEQ ID NO 2
<211> LENGTH: 18
```

```
<212> TYPE: DNA
<213> ORGANISM: Artificial Sequence
<220> FEATURE:
<223> OTHER INFORMATION: DNA sequence coding for peptide HHHHHH (6xHis)

<400> SEQUENCE: 2
caccatcacc atcaccac                                                    18

<210> SEQ ID NO 3
<211> LENGTH: 35
<212> TYPE: DNA
<213> ORGANISM: Artificial Sequence
<220> FEATURE:
<223> OTHER INFORMATION: oligonuclotide Q744R

<400> SEQUENCE: 3
ggaatacaag aagcctattc ggacgcgctt gaacc                                 35

<210> SEQ ID NO 4
<211> LENGTH: 35
<212> TYPE: DNA
<213> ORGANISM: Artificial Sequence
<220> FEATURE:
<223> OTHER INFORMATION: oligonuclotide Q744R anti

<400> SEQUENCE: 4
ggttcaagcg cgtccgaata ggcttcttgt attcc                                 35

<210> SEQ ID NO 5
<211> LENGTH: 35
<212> TYPE: DNA
<213> ORGANISM: Artificial Sequence
<220> FEATURE:
<223> OTHER INFORMATION: oligonuclotide Q744L

<400> SEQUENCE: 5
ggaatacaag aagcctattc tgacgcgctt gaacc                                 35

<210> SEQ ID NO 6
<211> LENGTH: 35
<212> TYPE: DNA
<213> ORGANISM: Artificial Sequence
<220> FEATURE:
<223> OTHER INFORMATION: oligonuclotide Q744L anti

<400> SEQUENCE: 6
ggttcaagcg cgtcagaata ggcttcttgt attcc                                 35

<210> SEQ ID NO 7
<211> LENGTH: 35
<212> TYPE: DNA
<213> ORGANISM: Artificial Sequence
<220> FEATURE:
<223> OTHER INFORMATION: oligonuclotide Q744P

<400> SEQUENCE: 7
ggaatacaag aagcctattc cgacgcgctt gaacc                                 35

<210> SEQ ID NO 8
<211> LENGTH: 35
<212> TYPE: DNA
<213> ORGANISM: Artificial Sequence
<220> FEATURE:
<223> OTHER INFORMATION: oligonuclotide Q744P anti

<400> SEQUENCE: 8
```
ggttcaagcg cgtcggaata ggcttcttgt attcc                                35

<210> SEQ ID NO 9
<211> LENGTH: 33
<212> TYPE: DNA
<213> ORGANISM: Artificial Sequence
<220> FEATURE:
<223> OTHER INFORMATION: oligonuclotide C510R

<400> SEQUENCE: 9
gcaagattct ccgttccgct tccttgcgtt ctg                                  33

<210> SEQ ID NO 10
<211> LENGTH: 33
<212> TYPE: DNA
<213> ORGANISM: Artificial Sequence
<220> FEATURE:
<223> OTHER INFORMATION: oligonuclotide C510R anti

<400> SEQUENCE: 10
cagaacgcaa ggaagcggaa cggagaatct tgc                                  33

<210> SEQ ID NO 11
<211> LENGTH: 38
<212> TYPE: DNA
<213> ORGANISM: Artificial Sequence
<220> FEATURE:
<223> OTHER INFORMATION: oligonuclotide S767G

<400> SEQUENCE: 11
cctaccatta acaccaacaa agatggcgag attgatgc                             38

<210> SEQ ID NO 12
<211> LENGTH: 38
<212> TYPE: DNA
<213> ORGANISM: Artificial Sequence
<220> FEATURE:
<223> OTHER INFORMATION: oligonuclotide S767G anti

<400> SEQUENCE: 12
gcatcaatct cgccatcttt gttggtgtta atggtagg                             38

<210> SEQ ID NO 13
<211> LENGTH: 48
<212> TYPE: DNA
<213> ORGANISM: Artificial Sequence
<220> FEATURE:
<223> OTHER INFORMATION: Oligonuclotide T7-Min

<400> SEQUENCE: 13
aattctaata cgactcacta tagtatgagg gcagcagaca tcgaattt                  48

<210> SEQ ID NO 14
<211> LENGTH: 48
<212> TYPE: DNA
<213> ORGANISM: Artificial Sequence
<220> FEATURE:
<223> OTHER INFORMATION: Oligonuclotide T7-plus

<400> SEQUENCE: 14
aaattcgatg tctgctgccc tcatactata gtgagtcgta ttagaatt                  48

<210> SEQ ID NO 15
<211> LENGTH: 33
<212> TYPE: DNA
<213> ORGANISM: Artificial Sequence
<220> FEATURE:
<223> OTHER INFORMATION: Balise molculaire MB1
<220> FEATURE:
<221> NAME/KEY: misc_binding
<222> LOCATION: (1)..(1)
<223> OTHER INFORMATION: FAM
<220> FEATURE:
<221> NAME/KEY: misc_binding
<222> LOCATION: (33)..(33)
<223> OTHER INFORMATION: Dabcyl

<400> SEQUENCE: 15
ctatcccttc gatgtctgct gccctcggga tag         33

<210> SEQ ID NO 16
<211> LENGTH: 883
<212> TYPE: PRT
<213> ORGANISM: Bacteriophage T7

<400> SEQUENCE: 16

```
Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
    290                 295                 300
```

```
Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
                325                 330                 335

Val Ala Asn Val Ile Thr Lys Trp Lys His Cys Pro Val Glu Asp Ile
            340                 345                 350

Pro Ala Ile Glu Arg Glu Leu Pro Met Lys Pro Glu Asp Ile Asp
        355                 360                 365

Met Asn Pro Glu Ala Leu Thr Ala Trp Lys Arg Ala Ala Ala Val
370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
                405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
        435                 440                 445

Gly Lys Pro Ile Gly Lys Glu Gly Tyr Tyr Trp Leu Lys Ile His Gly
450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
                485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
        515                 520                 525

Asn Cys Ser Leu Pro Leu Ala Phe Asp Gly Ser Cys Ser Gly Ile Gln
530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
                565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
        595                 600                 605

Val Lys Leu Gly Thr Lys Ala Leu Ala Gly Gln Trp Leu Ala Tyr Gly
610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
                645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
        675                 680                 685

Val Val Ala Ala Val Glu Ala Met Asn Trp Leu Lys Ser Ala Ala Lys
690                 695                 700

Leu Leu Ala Ala Glu Val Lys Asp Lys Thr Gly Glu Ile Leu Arg
705                 710                 715                 720
```

```
Lys Arg Cys Ala Val His Trp Val Thr Pro Asp Gly Phe Pro Val Trp
            725             730              735

Gln Glu Tyr Lys Lys Pro Ile Gln Thr Arg Leu Asn Leu Met Phe Leu
        740             745              750

Gly Gln Phe Arg Leu Gln Pro Thr Ile Asn Thr Asn Lys Asp Ser Glu
        755             760              765

Ile Asp Ala His Lys Gln Glu Ser Gly Ile Ala Pro Asn Phe Val His
    770             775              780

Ser Gln Asp Gly Ser His Leu Arg Lys Thr Val Val Trp Ala His Glu
785             790             795              800

Lys Tyr Gly Ile Glu Ser Phe Ala Leu Ile His Asp Ser Phe Gly Thr
            805             810              815

Ile Pro Ala Asp Ala Ala Asn Leu Phe Lys Ala Val Arg Glu Thr Met
            820             825              830

Val Asp Thr Tyr Glu Ser Cys Asp Val Leu Ala Asp Phe Tyr Asp Gln
        835             840              845

Phe Ala Asp Gln Leu His Glu Ser Gln Leu Asp Lys Met Pro Ala Leu
    850             855              860

Pro Ala Lys Gly Asn Leu Asn Leu Arg Asp Ile Leu Glu Ser Asp Phe
865             870             875              880

Ala Phe Ala
```

MUTATED T7 RNA POLYMERASES

The subject of the present invention is bacteriophage T7 mutated RNA polymerases, and the uses thereof.

The transcription phenomenon by which a molecule of RNA is synthesised by an RNA polymerase from a double-strand sequence of DNA is a fundamental biological mechanism. The T7 RNA polymerase enzyme is a DNA-dependent RNA polymerase coded by the genome of bacteriophage T7. The RNA polymerases of bacteriophages display a large degree of selectivity for their own promoter sequence. The T7 RNA polymerase binds specifically to the T7 promoter of the DNA strand which acts as the template for transcription.

The entire nucleotide sequence of bacteriophage T7 is known and the RNA polymerase of the phage (SEQ ID NO: 16) is coded by gene 1 of T7 polymerase (SEQ ID NO: 1). Other RNA polymerases similar to T7 RNA polymerase are RNA polymerases of the bacteriophages SP6 and T3. The T3 RNA polymerase exhibits a homology of approximately 80% with T7 RNA polymerase. Gene 1 of the T7 polymerase (SEQ ID NO: 1) has been cloned and expressed in bacteria, allowing the production of large amounts of the enzyme (Studier et al., U.S. Pat. No. 4,952,496). T7 polymerase is a monomeric protein with 883 amino acids (cf. SEQ ID NO: 16) having a molecular weight of 98.6 Kda. T7 RNA polymerase does not require additional factors in order to initiate transcription. The enzyme alone is capable of recognising its promoter, initiating transcription and elongating the RNA transcript. T7 RNA polymerase is particularly efficient and synthesises RNA five times quicker than the RNA polymerase of E. coli. Hence, the polymerases of bacteriophages are very useful due to their selectivity and activity in producing the transcripts (Lukaysky and Puglisi, RNA, 10: 889-893, 2004).

Specific mutants of RNA polymerases of T7-type bacteriophages have been described previously, in particular in order to understand the enzyme mechanism of T7 RNA polymerase (Gardner et al., Biochemistry, 36: 2908-2918, 1997; Nayak et al., JMB 371: 490-500, 2007). The document WO91/05866 describes systems of expression using the T7 bacteriophage promoter to manage the transcription of a cloned gene in bacteria. The system uses a T7 RNA polymerase truncated by the presence of one or more nucleotide deletions at the gene coding for T7 RNA polymerase. These deletions bring about a dephasing of the reading frame and generate a new stop codon. The U.S. Pat. No. 5,385,834 also describes a mutant of T7 RNA polymerase, characterised by the substitution of the glutamic acid in position 222 by a lysine. This mutant displays an alteration of the recognition of the T7 promoter, giving it the possibility of recognising sequence variations of the T7 promoter which are not normally recognised by wild T7 RNA polymerase.

Ikeda et al. (Ikeda, R. A. et al. Biochemistry, 31: 9073-9080, 1992 and Ikeda, R. A. et al., Nucl. Acid. Res., 20: 2517-2524, 1992) have described the use of two compatible plasmids which can be used to evaluate the efficiency of recognition of mutated promoter sequences of T7 RNA polymerase. The first plasmid carries gene 1 from the T7 RNA polymerase under the control of the E. coli tac promoter, whereas the second plasmid carries the gene which codes for the chloramphenicol acetyl transferase (CAT) gene under the control of the T7 promoter. The E. coli cells carrying these two plasmids are resistant to CAM (chloramphenicol) if the T7 polymerase recognises the T7 promoter and then transcribes the CAT gene from the second plasmid. If one or the other of the T7 promoter or T7 RNA polymerase is inactive, the CAT gene shall not be transcribed and the E. coli cells shall then be sensitive to CAM. Ikeda et al. have described the use of this two-plasmid system to study the effects of certain mutations either in the T7 promoter or in the T7 RNA polymerase enzyme.

In vitro transcription using RNA polymerases of phagic origin (for example T7 RNA polymerase, T3 RNA polymerase and SP6 RNA polymerase) has become a tool which is widely used in molecular biology (Beckert and Masquida, Methods Mol Bio, 703: 29-41, 2011). The first application is in vitro transcription alone as a tool intended to quickly produce large quantities of RNA transcripts. A second application consists in the use of RNA polymerases in nucleic acid amplification mechanisms. These methods are for example, NASBA, 3SR and TMA. In vitro transcription has also been described in combination with PCR as an additional linear amplification step after amplification by PCR (Compton, Nature, 350(7): 91-92, 1991; Deiman et al. Molecular Biotechnology, 20: 163-179, 2002; Gill and Ghaemi, Nucleosides, Nucleotides and nucleic acids, 27: 224-245, 2008). Hence, the invention has a preferred application in the field of diagnosis.

For all of the applications cited above, the use of higher amplification temperatures would be advantageous and would allow the kinetics of the transcription reaction to be improved. This advantage would be all the more pronounced for isothermal amplifications (NASBA, 3SR and TMA), thus improving the amplification efficiency of structured RNA targets. Applications in which the improvement of the transcription reaction kinetics is important pertain to the amplifications of long RNA sequences (>500 nucleotides) and multiplex reactions.

Hence, the document EP-B-1.137.781 describes RNA polymerases mutated at position 633 which originate from T7-type bacteriophage and which have an increased stability to high temperatures.

Likewise, document EP-B-1.261.696 describes thermostable T7 RNA polymerases mutated notably at position 430, 849 or 880 possibly combined with the preceding mutation at position 633.

An improvement in the thermostability is characterised in many cases by a reduction in the specific activity, in particular caused by a loss of flexibility in the structure (Daniel, R. M. Enzyme and Microbial Technology, 19(1): 74-79, 1996; Eijsink et al. Biomolecular engineering, 22: 21-30, 2005). The thermostable mutants described in this document have a specific activity of RNA transcript synthesis which is greatly reduced compared to the wild enzyme. The present invention also proposes to remedy this disadvantage.

RNA polymerases which are mutated and preferred according to the present invention are T7 RNA polymerases mutated at position 744, the glutamine (Q) in position 744 being replaced by an amino acid selected from arginine (Q744R), leucine (Q744L) or proline (Q744P). Such a mutation can be represented by the general formula Q744X, wherein X is an amino acid selected from arginine (R), leucine (L) or proline (P). Preferably, X represents arginine (R), which indicates that the glutamine (Q) in position 744 is replaced by arginine (Q744R).

In one particular embodiment, the T7 RNA polymerase comprises in addition to the mutation Q744 (Q744X) at least one of the following mutations: F849I (substitution of phenylalanine in position 849 by isoleucine), F880Y (substitution of phenylalanine in position 880 by tyrosine), S430P (substitution of serine in position 430 by proline).

Surprisingly, certain particular mutations have an increased specific activity compared to the specific activity of the wild RNA polymerase.

In one particular embodiment, the T7 RNA polymerase comprises the mutations Q744X, preferably Q744R, F849I, F880Y and S430P.

In another particular embodiment, the T7 RNA polymerase comprises the mutations Q744X, preferably Q744R, F849I, F880Y, S430P and S767G (substitution of the serine in position 767 by glycine).

In another particular embodiment, the T7 RNA polymerase comprises the mutations Q744X, preferably Q744R, F849I, F880Y, S430P and C510R (substitution of the cysteine in position 510 by arginine).

In another particular embodiment, the T7 RNA polymerase comprises the mutations Q744X, preferably Q744R, F849I, F880Y, S430P, C510R and S767G.

These mutated RNA polymerases therefore display both an increased thermostability and a very good level of specific activity. In fact, the mutation in position 744 makes it possible to improve or restore the specific level of activity deteriorated by the presence of thermostabilising mutations. Other mutations contributing to the gain in thermostability are K713E, T745K, K392M.

The mutations which are thermostabilising and/or which increase the specific activity have been isolated from libraries of T7 RNA polymerase variants constructed by random mutagenesis, by the association of a method of selecting suppressive mutations and the use of a two-plasmid system, in accordance with the techniques known to the person skilled in the art (Kotsuka, T. et al., *J. Bacteriology*, 178(3), p. 723-727, 1996. Hirano, N. et al. *Biochemistry*, 39, p. 13285-13294, 2000; Ikeda, R. A. et al. *Biochemistry*, 31, p. 9073-9080, 1992; Ikeda, R. A. et al. *Nucleic Acid Research*, 20, p. 2517-2524, 1992).

The present invention also relates to a gene coding a T7 RNA polymerase mutated according to the present invention.

Furthermore, the present invention also relates to an expression vector comprising a gene coding a T7 RNA polymerase mutated according to the present invention and the appropriate expression sequences.

To express a gene, the gene is placed under the control of regulating and promoter sequences which make it possible to express the protein coded by said gene. This is generally performed by cloning the gene to be expressed downstream of these regulatory and promoter sequences. These sequences may be promoter sequences which are bound to the gene in its native form. According to a variant, these may be heterologous promoters. An advantage of the use of heterologous promoters is that they offer the possibility of expressing the gene in the host cells which do not recognise the native promoter of the gene. Furthermore, the heterologous promoter may be a promoter which is inducible, such that the expression of the gene can be primed at any desired moment.

The promoter sequences are sequences to which the RNA polymerase binds, at the start of transcription. The promoter sequences depend on the type of cells which they come from. The promoter sequences have been described for the promoters of prokaryote, eukaryote and viral origin. The recombinant DNA molecules may, for example, be obtained by cutting a given DNA fragment with a suitable restriction enzyme, by cutting a fragment containing regulatory and promoter sequences with the same enzyme and by binding the two fragments in such a manner that the nucleic acid sequence to be expressed, namely a gene coding a T7 RNA polymerase according to the present invention, is controlled by the promoter sequence. A large number of approaches intended to make useful recombinants have been described in Sambrook (Sambrook et al., Molecular cloning, a laboratory manual. Cold Spring Laboratory Press, Cold Spring Harbor, N.Y. (1989)).

In general, the recombinant nucleic acid sequences shall be cloned in what is called a vector molecule. The recombinant vector molecule then formed, which is often capable of self-replication in a suitable host cell, may be used to transport the cloned nucleic acid sequences into a cell. It may be a cell inside which the replication of the recombinant vector molecule takes place. It may also be a cell inside which a promoter and regulatory sequence of the vector is recognised, such that an RNA polymerase mutated according to the present invention is expressed. A huge range of vectors is presently known, comprising vectors intended to be used in bacteria, for example, Pbr322, 325 and 328, various pUC vectors, for example pUC 8,9,18,19, specific expression vectors: pGEM, pGEX, and Bluescript®, vectors based on bacteriophages; lambda-gtWes, Charon 28, phages derived from M13, expression vectors, in eukaryote cells containing viral sequences based on SV40, the papillomavirus, adenovirus or polyomavirus (Rodrigues, R. L. and Denhardt, D. T., ed; Vectors: A survey of molecular cloning vectors and their uses, Butterworths (1988), Lenstra et al., Arch. Virol.; 110:1-24 (1990)). All of the recombinant molecules comprising the nucleic acid sequence controlled by regulatory and promoter sequences allowing the expression of mutated RNA polymerase are considered to be part of the present invention.

The invention further comprises a host or transformed cell including a nucleic acid sequence which codes for RNA polymerase mutated according to the invention, or a molecule of recombinant nucleic acid which codes for mutated RNA polymerase controlled by regulatory and promoter sequences allowing the expression of mutated RNA polymerase.

Frequently used expression systems are the expression systems of cells from bacteria, yeasts, fungi, insects and mammals. These systems are well known to the person skilled in the art and are easily available for example on the market from Clontech Laboratories, Inc. 4030 Fabian Way, Palo Alto, Calif., 94303-4607, USA.

A host cell may be a bacteria cell, for example of *Escherichia coli, Bacillus subtilis* and the *Lactobacillus* species, in combination with vectors based on bacteria such as pBR322, or bacterial expression vectors such as pGEX, or with bacteriophages. The host cell may also be of eukaryote origin, for example, yeast cells in combination with specific vector molecules of yeast, or higher eukaryote cells such as insect cells (Luckow et al.; Biotechnology 6: 47-55 (1988)) in combination with vectors or recombinant baculovirus, vegetable cells in combination with, for example, vectors based on the Ti plasmid or plant viral vectors (Barton, K. A. et al.; Cell 32: 1033 (1983)), mammalian cells such as Hela cells, Chinese Hamster Ovary (CHO) or Crandell feline kidney cells, also combined with suitable recombinant vectors or viruses.

Hence, an expression vector comprising a gene coding for an RNA polymerase according to the invention and suitable promoter and regulatory sequences of expression are also part of the present invention, as well as the host cells transformed with these.

The mutated RNA polymerases according to the invention have applications in all the processes in which the RNA polymerases are used normally or at elevated temperatures. The use of the RNA polymerases according to the invention offers the advantage of obtaining improved stability and specificity.

The mutated RNA polymerases according to the invention are particularly useful in the processes of isothermal amplification by nucleic acid transcription.

The techniques of amplification by transcription involve the transcription of multiple RNA copies from a template comprising a promoter recognised by an RNA polymerase. With these methods, the multiple copies of RNA are transcribed from a DNA template which comprises a functional promoter recognised by the RNA polymerase. Said copies are used as targets from which a further quantity of the DNA template is obtained, etc. These methods have been described by Gingeras et al. in patent application WO88/10315 and by Burg et al. in patent application WO89/1050. Techniques of isothermal amplification by transcription were described by Davey et al. in patent EP-B-0.329.822 (pertaining to the NASBA method), by Gringeras et al. in patent EP-B-0.373.960 and by Kacian et al. in patent EP-B-0.408.295. The transcription amplification reactions may also be performed with thermostable enzymes. Transcription amplifications are generally performed at a temperature of around 37 to 41° C. These thermostable enzymes make it possible to perform the reaction at higher temperatures (>41° C.). Such a thermostable method is described in patent EP-B-0.682.121 filed in the name of Toyo Boseki.

The methods as described in patents EP-B-0.329.822, EP-B-0.373.960 and EP-B-0.408.295 are continuous isothermal methods. With these methods, four enzymatic activities are required to perform amplification: an RNA-dependent DNA polymerase activity, a DNA-dependent DNA polymerase activity, an RNase(H) activity and an RNA polymerase activity. Some of these activities can be combined in one enzyme, and therefore, generally, only two or three enzymes will be necessary. The enzymes having RNA-dependent DNA polymerase activities are enzymes which synthesise DNA from an RNA template. A DNA-dependent DNA polymerase synthesises DNA from a DNA template. In the transcription amplification reactions, a reverse transcriptase such as AMV (Avian Myeloblastoma Virus) or MMLV (Moloney Murine Leukemia Virus) reverse transcriptase may be used for these activities. These enzymes have a DNA polymerase activity which is both RNA- and DNA-dependent, and also exhibit an inherent RNase H activity. Furthermore, an RNase H can be added to the reaction mixture of a transcription amplification reaction, such as RNase H and *E. coli*.

The RNA polymerase which is commonly used with the transcription amplification methods is T7 RNA polymerase. Thus, the promoter which is incorporated in the template used for the transcription of multiple RNA copies is often the T7 promoter. Generally, the template comprising the promoter is created starting with the nucleic acid comprising the target sequence. The nucleic acid present in the starting material will generally contain the target sequence as part of a much longer sequence. Additional nucleic acid sequences may be present on the 3' end and 5' end of the target sequence. The amplification reaction may be primed by bringing together this nucleic acid present in the starting material, the suitable enzymes which jointly provide the abovementioned activities and at least one, but generally two, oligonucleotide(s). At least one of these oligonucleotides would have to comprise the promoter sequence.

The transcription amplification methods are particularly useful if the starting material is single-strand RNA, although single-strand or double-strand DNA may also be used as input material. When a transcription amplification method is performed on a sample with single-strand RNA ("plus" sense) with additional sequences on the 3' and 5' ends of the target sequence, a pair of oligonucleotides which is properly used with the methods such as described in the prior art would be made up of:

a first oligonucleotide (which is generally referred to as "the promoter oligonucleotide") which is capable of hybridisation at the 3' end of the target sequence, said oligonucleotide has the sequence of a promoter (preferably of the T7 promoter) bound to its 5' end (the hybridisation part of this oligonucleotide has opposite polarity to that of RNA plus, used as starting material), a second oligonucleotide ("primer") which is made up of the 3' end of the target sequence (this oligonucleotide has the same polarity as RNA plus).

When a pair of oligonucleotides (together with all of the enzymes of suitable activity) and a sufficient supply of necessary ribonucleotides and deoxyribonucleotides are placed together in a reaction medium and kept in suitable conditions (i.e. in suitable buffer conditions and at the suitable temperature) for a sufficient duration, a continuous and isothermal amplification reaction will occur.

Another object of the invention therefore pertains to at least one oligonucleotide (or a mixture of oligonucleotides) of sequence SEQ ID NO: 3, SEQ ID NO: 4, SEQ ID NO: 5, SEQ ID NO: 6, SEQ ID NO: 7, or SEQ ID NO: 8 in order to obtain, preferably by directed mutagenesis, a gene coding a T7 RNA polymerase mutated according to the invention and therefore to generate in fine a T7 ARN polymerase mutated according to the invention.

Preferably, the above-mentioned oligonucleotides (which are usable as primers) are used in pairs (sense oligonucleotide/anti-sense oligonucleotide) and the invention therefore pertains to a pair of oligonucleotides comprising a first oligonucleotide and a second oligonucleotide, said pair of oligonucleotides being selected from the following pairs of oligonucleotides:

a first oligonucleotide of sequence SEQ ID NO: 3 and a second oligonucleotide of sequence SEQ ID NO: 4 (making it possible to generate the mutation Q744R), a first oligonucleotide of sequence SEQ ID NO: 5 and a second oligonucleotide of sequence SEQ ID NO: 6 (making it possible to generate the mutation Q744L), a first oligonucleotide of sequence SEQ ID NO: 7 and a second oligonucleotide of sequence SEQ ID NO: 8 (making it possible to generate the mutation Q744P).

Preferably, the mutants of T7 RNA polymerase are constructed by directed mutagenesis, for example directly on the vector derived from pMR-7-cas, by using at least one oligonucleotide or, preferably, at least one pair of oligonucleotides according to the invention.

Advantageously, the method used to generate these mutants is the one described by the protocol of the Quickchange® kit from Stratagene (Ref. 200518) and is performed with the pfu Ultra HF polymerase from Stratagene.

The present invention also pertains to the use of at least one oligonucleotide or, preferably, of at least one pair of oligonucleotides according to the invention to obtain a gene coding a T7 RNA polymerase mutated according to the invention (preferably by directed mutagenesis) and therefore to generate in fine a T7 ARN polymerase mutated according to the invention.

The RNA polymerases according to the invention may also be used together with other processes for amplification of nucleic acids. In polymerase chain amplification (PCR), primers are sometimes used in which a promoter sequence of a bacteriophage RNA polymerase, in particular the T7 RNA polymerase promoter sequence, has been incorporated. This allows the transcription of RNA to form the DNA product of the PCR reaction. Here again, the RNA polymerases according to the invention may also be used.

Hence, a mixture of enzymes intended to be used in a transcription isothermal amplification reaction comprising an RNA polymerase such as proposed according to the present invention, one enzyme having a reverse transcriptase activity and one enzyme having an RNase H activity, is also part of the present invention.

The invention will be illustrated further by the following examples.

EXAMPLE 1

Method of Producing and Purifying T7 RNA Polymerase Mutants

1/Plasmid Constructions for the Expression of Recombinant T7 RNA Polymerase Proteins The expression plasmid of T7 RNA polymerase is a derivative of the vector pMR-7cas (Arnaud et al. 1997, Gene 199: 149-156).

The DNA sequences coding for the recombinant proteins of interest were introduced into the expression vector derived from pMR-7-cas between the BamHI and XbaI restriction sites.

A poly-Histidine sequence (6xHis) is present in the N-terminus position of T7 RNA polymerase to allow it to be purified on a metal chelate affinity column. It is a binding region on the Ni-NTA gel which makes it possible to subsequently facilitate the recombinant protein purification step. This poly-Histidine sequence is coded by the sequence CAC CAT CAC CAT CAC CAC (SEQ ID NO:2).

The wild sequence of gene 1 of T7 RNA polymerase corresponding to the sequence described by the NCBI entry number NC 001604 is the sequence SEQ ID NO: 1.

2/Method for Producing Single and Combined Mutants of T7 RNA Polymerase

The mutants of T7 RNA polymerase were constructed by directed mutagenesis directly on the vector derived from pMR-7-cas.

The method used to generate the single and combined mutants is described by the protocol for the Quickchange® kit from Stratagene (Ref. 200518) and is performed with the pfu Ultra HF polymerase from Stratagene.

The oligonucleotides used to generate the mutations Q744R, Q744P, C510R and S767G are the following:

```
SEQ ID NO: 3    oligonucleotide Q744R GGAATACAAGAAGCCTATTCGGACGCGCTTGAACC

SEQ ID NO: 4    oligonucleotide Q744R GGTTCAAGCGCGTCCGAATAGGCTTCTTGTATTCC
                anti SEQ ID NO: 5    oligonucleotide Q744L GGAATACAAGAAGCCTATTCTGACGCGCTTGAACC SEQ ID NO: 6    oligonucleotide Q744L GGTTCAAGCGCGTCAGAATAGGCTTCTTGTATTCC
                anti SEQ ID NO: 7    oligonucleotide Q744P GGAATACAAGAAGCCTATTCCGACGCGCTTGAACC SEQ ID NO: 8    oligonucleotide Q744P GGTTCAAGCGCGTCGGAATAGGCTTCTTGTATTCC
                anti SEQ ID NO: 9    oligonucleotide C510R GCAAGATTCTCCGTTCCGCTTCCTTGCGTTCTG SEQ ID NO: 10   oligonucleotide C510R CAGAACGCAAGGAAGCGGAACGGAGAATCTTGC
                anti SEQ ID NO: 11   oligonucleotide S767G CCTACCATTAACACCAACAAAGATGGCGAGATTGATGC SEQ ID NO: 12   oligonucleotide S767G GCATCAATCTCGCCATCTTTGTTGGTGTTAATGGTAGG
                anti
```

The combined mutants are obtained iteratively or by substitution of fragments of the T7 RNA polymerase sequence.

3/Expression of Recombinant Proteins of T7 RNA Polymerase:

A plasmid construction comprising a mutant sequence of T7 RNA polymerase is inserted into the expression vector derived from pMR-7-cas used to transform an *E. coli* bacteria (strain BL21) in accordance with a conventional protocol known to the person skilled in the art (Molecular Cloning—A laboratory—1.74, 1989, Sambrook Joseph, E F. Fritsch, T. Maniatis 2nd Edition, ISBN 0-87969-309-6).

The transformed bacteria are selected due to their resistance to ampicillin borne by the vector derived from pMR-7-cas. The protocol for producing the recombinant proteins is described below:
1. A colony is inoculated in 10 mL of Luria Broth (LB) medium containing 100 mg/mL of ampicillin at 30° C. for 16 h under agitation at 220 rpm (pre-culture)
2. 3.3 mL of the pre-culture are used to seed 200 mL of LB medium to obtain a final OD at 600 nm of between 0.07 and 0.09. The medium is then grown at 37° C. under agitation (220 rpm)
3. When the OD at 600 nm of the culture has reached a value of between 0.4 and 0.6, the overexpression of the T7 RNA polymerase recombinant proteins is induced by the addition of IPTG at the final concentration of 0.4 mM. The culture medium is then agitated (220 rpm) for 4 h at 37° C.

4/Method of Purifying the T7 RNA Polymerase Mutants
1. 200 mL of *E. coli* culture are centrifuged (20 mins, 4° C., 6000 g) and the biomass obtained is suspended in 10 mL of lysis buffer (50 mM Tris-HC pH 8.0, 300 mM NaCl)
2. The preceding cell suspension is lysed by 5 sonication cycles of 30 seconds each
3. The lysate from step [2.] is centrifuged at 22000 g for 2 mins at 4° C.
4. The preceding supernatant is purified by affinity chromatography on a metal chelate column. To do this, it is deposited on a 1 mL Ni-NTA column (His Trap™, GE Healthcare, ref. 17-5247) balanced beforehand with the same lysis buffer at ambient temperature. The column is then washed with 10 mL of the same buffer. The elution of the recombinant protein is obtained by applying 5 mL of elution buffer (50 mM Tris-HC pH 8.0, 200 mM NaCl, 200 mM imidazole) and recovering 0.5 mL fractions
5. The production level and the purity of the recombinant proteins are controlled by analysis on SDS-PAGE 10% gel and staining with Coomassie blue
6. The measurement of the concentrations of purified T7 RNA polymerase proteins is carried out in accordance with the method described by Bradford with the aid of the Bradford Quick Start™ kit from BioRad (Bradford, M. 1976, "Rapid and sensitive method for the quantitation of microgram quantities of protein utilizing the principle of protein-dye binding", *Anal. Biochem.* 72: 248-254). The standard used to measure the recombinant protein concentration is BSA
7. The fraction containing the recombinant protein is desalted on a 7 kDa Zeba™ Desalt Spin column (Thermoscientific, ref. 89882) and taken up in a storage buffer (20 mM KH2PO4/K2HPO4 pH 7.5, 100 mM NaCl, 1M trehalose, 1 mM EDTA, 0.268% v/v Triton X-100, 0.1 mg/mL BSA, 1 mM DTT). Each purified T7 RNA polymerase mutant is stored at −80° C.

EXAMPLE 2

Measurement of the Specific Activity of the T7 RNA Polymerase Mutants

The methods of measuring the transcription mechanism are historically based on monitoring the incorporation of radioactivity into the newly formed transcript over time (Martin C. T. and Coleman E. Biochemistry, 26: 2690-2696, 1987). This approach has the disadvantage of measuring the T7 RNA polymerase activity which leads to the production of complete transcripts but also to the production of incomplete transcripts when the catalytic cycle of T7 RNA polymerase is abortive (Martin C. T. et al. Biochemistry 27: 3966-3974, 1988). Alternative methods have been developed which do not use radioactivity. These utilise fluorescent molecules such as RNA intercalators or molecular markers (Liu J. et al. Analytical Biochemistry, 300: 40-45, 2002) or colorimetric methods (Lee et al. Bull. Korean Chem Soc 30(10): 2485-2488, 2009). The approach based on the use of molecular markers has the advantage of specifically measuring the appearance of complete transcripts and not taking into account abortive cycles of T7 RNA polymerase leading to the generation of small incomplete transcripts.

In this example, the specific activities of several mutants of T7 RNA polymerase are determined with the aid of molecular markers. A description of the measurement method is presented below, as well as the different reagents used.

| Buffer A | Buffer B | Buffer C | Buffer D |
|---|---|---|---|
| 20 mM KH2PO4/K2HPO4, pH 7.5 100 mM NaCl Trehalose between 0.5 and 1M 1 mM EDTA 0.268% (v/v) Triton X-100 0.1 mg/mL BSA 1 mM DTT | 20 mM Tris-HCl, pH 7.5 300 mM KCl Trehalose between 0.5 and 1M 7 mM EDTA 0.21% (w/v) Triton X-100 0.2 mg/mL BSA 1 mM DTT 20 mM Magnesium acetate | 200 mM KH2PO4/K2HPO4, pH 7.2 Trehalose between 0.5 and 1M 0.21% (w/v) Triton X-100 1 mM DTT | 3.2 mM Tris-HCl, pH 7.5 6.4 mM NaCl 0.13 mM DTT 1.3 mg/mL BSA Trehalose between 0.1 and 0.5 mM |

Solution W:

Mix buffers A, B, C and D in accordance with the following proportions:

10% buffer A 1.8% buffer B

7% buffer C 35.7% buffer D 45.6% water for molecular biology.

Solution S (Substrate Mix):
70 mM Tris-HCl, pH 8.5
1.3 mM dNTP each
2.6 mM rATP, rCTP and rUTP each
2 mM rGTP
0.6 mM rITP
60 mM saccharose
40 mM mannitol
7 g/L Dextran T-40
16 mM MgCl2
320 mM KCl
20 mM DTT
3.5 M DMSO
Molecular marker MB1 between 0.1 and 0.3 µM
Oligonucleotide T7-Min between 10 and 20 nM
Oligonucleotide T7-plus between 10 and 20 nM
Sequences Used (Orientation 5'→3'):

```
SEQ ID NO: 13; T7-min   AATTCTAATACGACTCACTATAGTATGAGGGCAGCAGACATCGAATTT

SEQ ID NO: 14; T7-plus  AAATTCGATGTCTGCTGCCCTCATACTATAGTGAGTCGTATTAGAATT

SEQ ID NO: 15; MB1      FAM-CTATCCCTTCGATGTCTGCTGCCCTCGGGATAG-Dabcyl
```

The protocol for measuring T7 RNA polymerase volumetric activity is described below:
1. Diluting the T7 RNA polymerase enzyme in buffer A in order to obtain a 1 mg/mL enzyme solution
2. 5 µL of the 1 mg/mL enzyme solution are diluted in 39 µL of solution W
3. 5 µL of the preceding solution [2.] are diluted in 50 µL of solution W
4. 25 µL of the preceding solution [3.] are added to 75 µL of solution S
5. 20 µL of the preceding solution [4.] are used to measure the activity at 37° C. for 30 mins.

The FAM fluorescence generated by the association of molecular markers and the accumulation of the transcripts produced by the T7 RNA polymerase activity is monitored with the aid of an EASY-Q™ fluorometer from bioMérieux. The linear increase in the fluorescence between 5 and 10 mins makes it possible to calculate a reaction speed which can be directly correlated to the volumetric activity of the enzyme by use of a standard T7 RNA polymerase with the known volumetric activity. The ratio of speeds between the standard and the mutant makes it possible to obtain the unknown volumetric activity value. The T7 RNA polymerase volumetric activity is expressed in kU/mL of enzyme and corresponds to the quantity of RNA transcripts recognised by the molecular markers per unit of time (minutes) and per unit of enzyme volume (milliliters). The specific activity (SA) of the mutant is expressed in kU/mg and corresponds to the normalisation of the volumetric activity by the enzyme protein concentration.

Calculation of Volumetric Activity:
$p_r$=gradient obtained between 5 and 10 mins for the reference T7 RNA polymerase
$p_x$=gradient obtained between 5 and 10 mins for the T7 RNA polymerase mutant
$A_r$=volumetric activity of the reference T7 RNA polymerase
$A_x$=volumetric activity of the mutant T7 RNA polymerase $$A_x = (A_r * p_x)/p_r$$

The gross values of the gradients must be between 0.3 and 0.8 to accept the final value of the calculated volumetric activity. Outside of this range, the initial sample must be diluted in buffer 1 so as to be within the tolerated measurement range.

The results of the specific activity measurement at 37° C. of the T7 RNA polymerase mutants are described in Table 1:

TABLE 1

Specific activity values of the T7 RNA polymerase mutants measured at 37° C. T3 corresponds to the triple mutant comprising the mutations S430P + F880Y + F849I (called either "T3" or "Q3" within the present patent application) and Q4 corresponds to the quadruple mutant T3 + S633P.

| T7 RNA polymerases | SA 37° C. (kU/mg) |
|---|---|
| WT | 570.8 |
| Q744R | 664.0 |

TABLE 1-continued

Specific activity values of the T7 RNA polymerase mutants measured at 37° C. T3 corresponds to the triple mutant comprising the mutations S430P + F880Y + F849I (called either "T3" or "Q3" within the present patent application) and Q4 corresponds to the quadruple mutant T3 + S633P.

| T7 RNA polymerases | SA 37° C. (kU/mg) |
|---|---|
| Q744P | 793.1 |
| Q744L | 819.1 |
| C510R | 73.9 |
| S767G | 300.5 |
| T3 | 421.8 |
| Q4 | 110.4 |
| T3 + Q744R | 846.5 |
| T3 + Q744L | 781.6 |
| T3 + Q744P | 548.2 |
| T3 + C510R | 126.8 |
| T3 + S767G | 374.1 |
| T3 + C510R + S767G | 79.6 |
| T3 + C510R + Q744R | 519.2 |
| T3 + S767G + Q744R | 700.3 |
| T3 + Q744R + C510R + S767G | 336.2 |

Conclusion

Thus, the T7 RNA polymerases mutated at position 744 (Q744R, Q744P or Q744L) have an increased specific activity compared to the specific activity of the wild T7 RNA polymerase. The T7 RNA polymerases comprising the mutations S430P+F880Y+F849I (T3), or S430P+F880Y+F849I+C510R (T3+C510R) or S430P+F880Y+F849I+S767G (T3+S767G) or S430P+F880Y+F849I+C510R+S767G (T3+C510R+S767G) exhibit an increased thermostability due to their improved half-life temperatures $T_{1/2}$ (Table 2) but also a low specific activity as shown in Table 1. These same T7 RNA polymerases which further comprise the mutation Q744R have both a sustained thermostability and a very good specific activity. Thus, the mutation Q744R allows an improvement in, or even a restoration of, the specific activity altered by the thermostabilising mutations.

EXAMPLE 3

Measurement of the Half-Life Temperature ($T_{1/2}$) of the T7 RNA Polymerase Mutants after 10 Mins of Denaturation at Different Temperatures In this example, the $T_{1/2}$ values of several mutants of T7 RNA polymerase are determined. A description of the measurement method is presented below, as well as the different reagents used.

| Buffer B | Buffer C | Buffer D |
|---|---|---|
| 20 mM Tris-HCl, pH 7.5 | 200 mM KH2PO4/K2HPO4, pH 7.2 | 3.2 mM Tris-HCl, pH 7.5 |
| 300 mM KCl | Trehalose between 0.5 and 1M | 6.4 mM NaCl |
| Trehalose between 0.5 and 1M | 0.21% (w/v) Triton X-100 | 0.13 mM DTT |
| 7 mM EDTA | 1 mM DTT | 1.3 mg/mL BSA |
| 0.21% (w/v) Triton X-100 | | Trehalose between 0.1 and 0.5M |
| 0.2 mg/mL BSA | | |
| 1 mM DTT | | |
| 20 mM Magnesium acetate | | |

Solution W1:
Mix buffers B, C and D in accordance with the following proportions:
1.8% buffer B
7% buffer C
38.6% buffer D
52.6% water for molecular biology.

Solution W2:
Dilute a reagent accusphere from the Nuclisens EasyQ™ VIH-1 1.2 kit produced by the bioMérieux company in 120 µL of diluent (kit reference, 285036) and 60 µL of water for molecular biology.

Solution W3:
Mix 1 volume of solution W1 to 3 volumes of solution W2.

Solution S (Substrate Mix):
70 mM Tris-HCl, pH 8.5
1.3 mM dNTP each
2.6 mM rATP, rCTP and rUTP each
2 mM rGTP
0.6 mM rITP
60 mM saccharose
40 mM mannitol
7 g/L Dextran T-40
16 mM MgCl2
320 mM KCl
20 mM DTT
3.5 M DMSO
Molecular marker MB1 between 0.1 µM and 0.3 µM
Oligonucleotide T7-min between 10 nM and 20 nM
Oligonucleotide T7-plus between 10 nM and 20 nM.

Sequences Used (Orientation 5'→3'):

```
SEQ ID NO: 13; T7-min   AATTCTAATACGACTCACTATAGTATGAGGGCAGCAGACATCGAATTT

SEQ ID NO: 14; T7-plus  AAATTCGATGTCTGCTGCCCTCATACTATAGTGAGTCGTATTAGAATT

SEQ ID NO: 15; MB1      FAM-CTATCCCTTCGATGTCTGCTGCCCTCGGGATAG-Dabcyl
```

1. The enzymes to be evaluated are diluted so as to have a volumetric activity of 84 kU/mL
2. 3 µL of the enzyme to be evaluated are diluted in 193 µL of solution 3
3. 7 20 µL portions of [2.] are divided into 0.2 mL tubes and incubated at the appropriate temperature in a thermocycler for 10 mins
4. 5 µL of the pre-incubated mixture are added to 20 µL of solution S in order to measure the rate of fluorescence increase between 5 and 10 mins associated with the enzyme's residual activity
5. The residual activity of each mutant is expressed as a percentage of the fraction of enzyme which has not been pre-incubated and which corresponds to 100% activity in accordance with the following calculation:

$p_N$=gradient obtained between 5 and 10 mins for the T7 RNA polymerase not preincubated $p_T$=gradient obtained between 5 and 10 mins for the mutant T7 RNA polymerase pre-incubated at different temperatures % relative activity=% $(p_T/p_N)$ 6. The $T_{1/2}$ value corresponds to the temperature at which the enzyme only has 50% of its initial volumetric activity without pre-incubation left The $T_{1/2}$ measurement results of the T7 RNA polymerase mutants are described in Table 2:

TABLE 2

$T_{1/2}$ temperature values of the T7 RNA polymerase mutants after 10 mins of pre-incubation at different temperatures.

| T7 RNA polymerase | $T_{1/2}$, °C. (10 mins of pre-incubation) |
|---|---|
| WT | 43.3 |
| Q744R | 43.5 |
| Q744P | 45.2 |
| Q744L | 44.6 |
| C510R | 44.4 |
| S767G | 44.0 |
| T3 (F880Y + S430P + F849I) | 49.2 |
| Q4 (T3 + S633P) | 50.2 |
| T3 + Q744R | 49.0 |
| T3 + Q744L | 49.4 |
| T3 + Q744P | 49.2 |
| T3 + C510R | 51.0 |
| T3 + S767G | 50.5 |
| T3 + C510R + S767G | 52.8 |
| T3 + C510R + Q744R | 51.0 |
| T3 + S767G + Q744R | 50.0 |
| T3 + Q744R + C510R + S767G | 51.2 |

Conclusion:

Table 2 thus makes it possible to demonstrate the quasi-neutrality of the Q744R mutation with respect to the thermostability of the various T7 RNA polymerase mutants described. When this mutation is added to a thermostable mutant, it does not markedly alter the $T_{1/2}$ value of the latter. Moreover, it is noted that the thermostabilising effects of the mutations C510R and S767G are additive when they are combined in the same T3 mutant.

EXAMPLE 4

NASBA Isothermal Amplification with the Improved Mutants of T7 RNA Polymerase In this example, the improved clones of T7 RNA polymerase were evaluated within the framework of NASBA amplification VIH1 1.2 from bioMérieux in order to confirm their functionality at temperatures higher than the reference temperature of 41° C. A description of the measurement method is presented below, as well as the different reagents used.

| Buffer B | Buffer C | Buffer D |
|---|---|---|
| 20 mM Tris-HCl, pH 7.5 | 200 mM KH2PO4/K2HPO4, pH 7.2 | 3.2 mM Tris-HCl, pH 7.5 |
| 300 mM KCl | | 6.4 mM NaCl |
| Trehalose between 0.5 and 1M | Trehalose between 0.5 and 1M | 0.13 mM DTT |
| 7 mM EDTA | | 1.3 mg/mL BSA |
| 0.21% (w/v) Triton X-100 | 0.21% (w/v) Triton X-100 | Trehalose between 0.1 and 0.5M |
| 0.2 mg/mL BSA | 1 mM DTT | |
| 1 mM DTT | | |
| 20 mM Magnesium acetate | | |

Solution W1:
Mix buffers B, C and D in accordance with the following proportions:
1.8% buffer B
7% buffer C
38.6% buffer D
52.6% water for molecular biology.
Solution E
Mix 16.4 µL of solution W1 with 3.14 µL of 25 U/µL AMV-RT, 0.79 µL of 1.2 U/µL RNAseH and 4.49 µL of water for molecular biology. This solution is frozen directly in liquid nitrogen and freeze-dried to produce a sphere (enzyme sphere) containing the enzyme mixture without T7 RNA polymerase activity.
The NASBA HIV1 1.2 amplification test is carried out on type-B VIH1 transcripts and in accordance with the recommendations of the manufacturer bioMérieux with the exception of the enzyme sphere ingredient enzyme which is replaced by the previously described solution E.

The protocol used is as follows and corresponding to a NASBA amplification reaction:
1. A reagent sphere from the HIV1 1.2 kit (kit reference, 285036) is dissolved in 90 µL of reagent diluent
2. An enzyme sphere corresponding to solution E is dissolved in 40.5 µL of enzyme diluent. To this solution are added 4.5 µL of the T7 RNA polymerase variant to be evaluated and of which the volumetric activity is between 70 and 120 kU/mL.
3. 5 µL of type-B HIV transcript corresponding to 5 cp/reactions or 20 cp/reactions are introduced into a 0.2 µL tube. 15 µL of reagent [1.] are then added, as well as 5 µL of enzyme solution [2.]
4. The reaction is carried out at 41° C. or greater in an EASYQ™ fluorometer from bioMérieux for 30 mins.

Figure 1A:
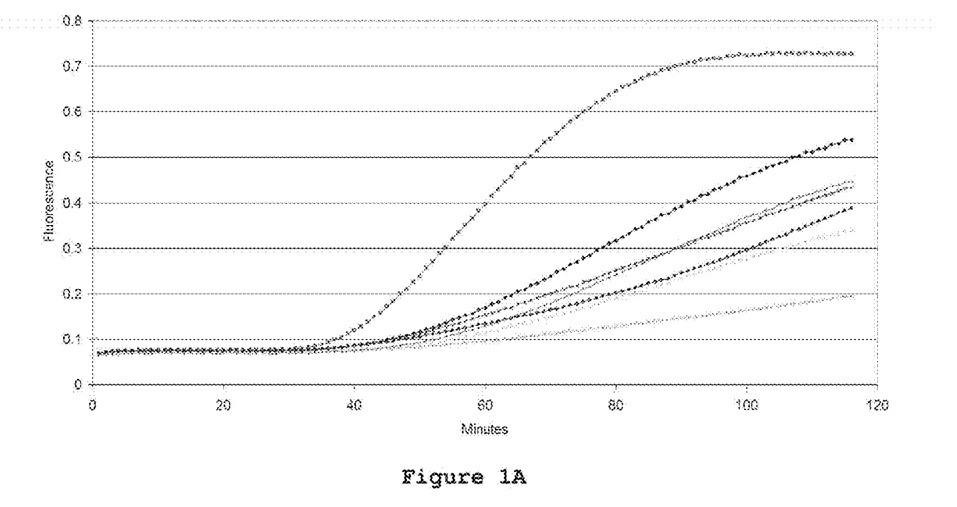
FIG. 1A: NASBA amplification HIV1 1.2 at 41° C. with wild T7 RNA polymerase (5 cp VIH1-B/trials; 7 technical replicates)
Figure 1B:
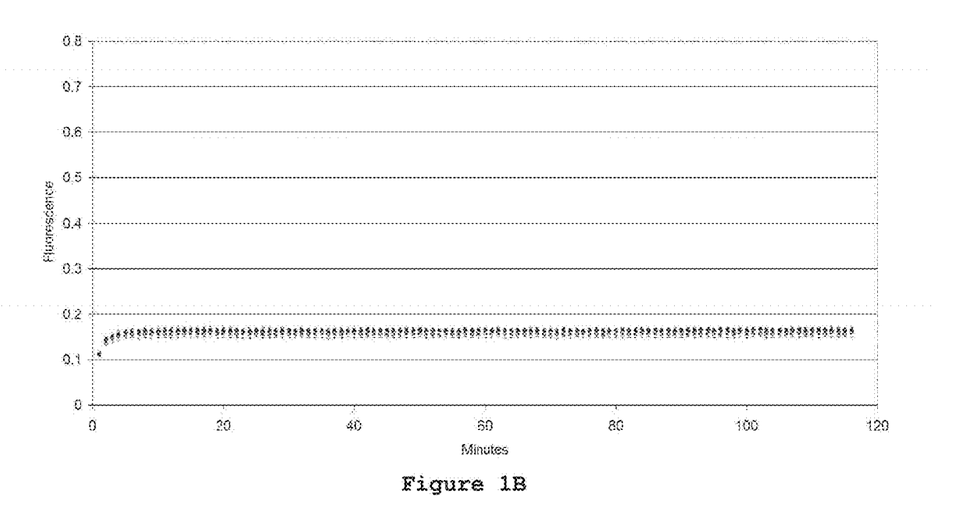
FIG. 1B: NASBA amplification HIV1 1.2 at 47° C. with wild T7 RNA polymerase (20 cp VIH1-B/trials; 7 technical replicates)
Figure 1C:
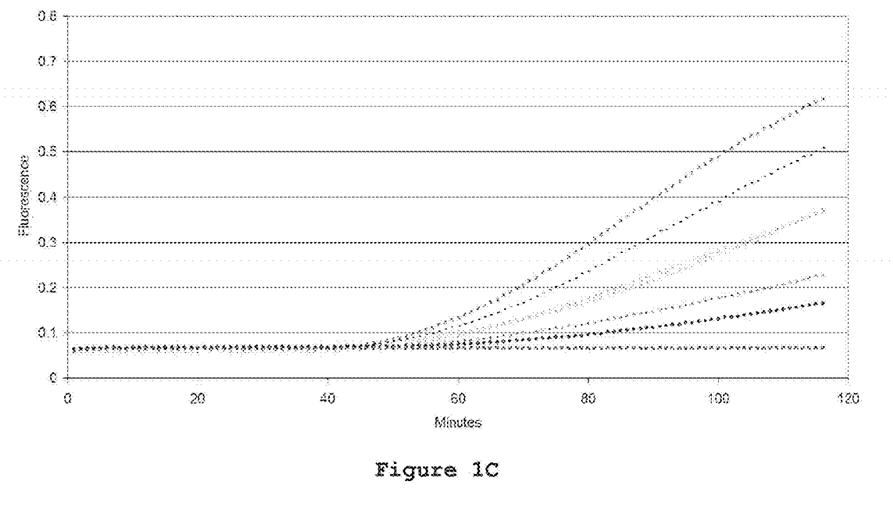
FIG. 1C: NASBA amplification HIV1 1.2 at 41° C. with T7 RNA polymerase Q3+Q744R (20 cp VIH1-B/trials; 7 technical replicates)
Figure 1D:
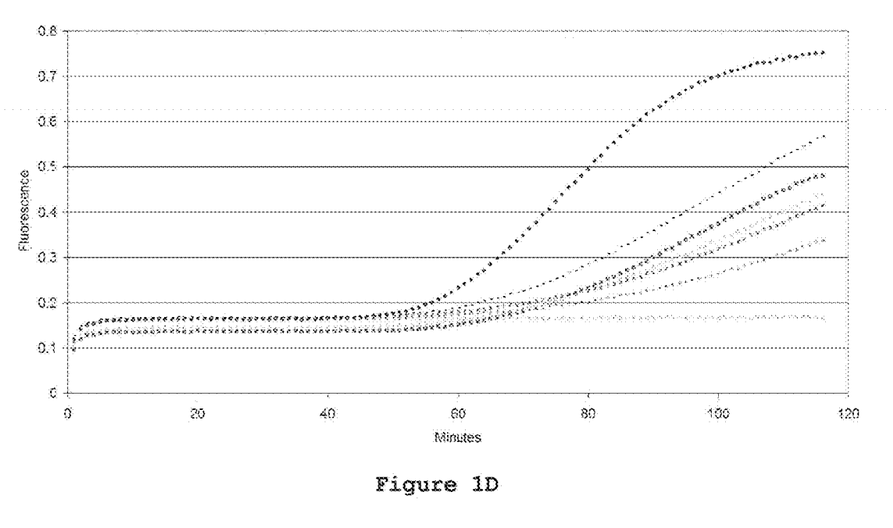
FIG. 1D: NASBA amplification HIV1 1.2 at 47° C. with T7 RNA polymerase Q3+Q744R (20 cp VIH1-B/trials; 7 technical replicates)
Figure 1E:
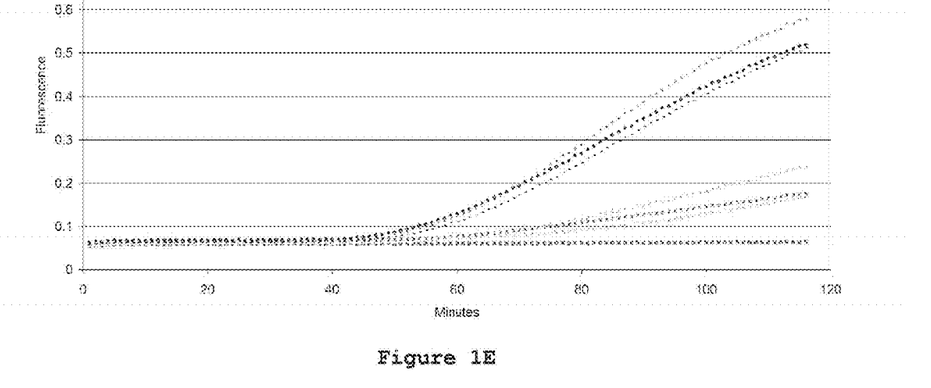
FIG. 1E: NASBA amplification HIV1 1.2 at 41° C. with T7 RNA polymerase Q3+Q744R+C510R (20 cp VIH1-B/trials; 7 technical replicates)
Figure 1F:
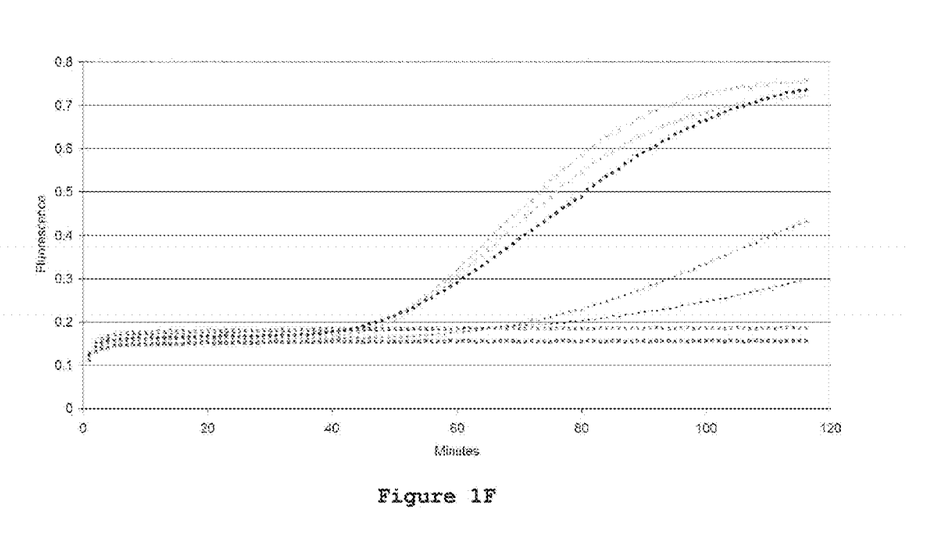
FIG. 1F: NASBA amplification HIV1 1.2 at 47° C. with T7 RNA polymerase Q3+Q744R+C510R (20 cp VIH1-B/trials; 7 technical replicates)
Figure 1G:
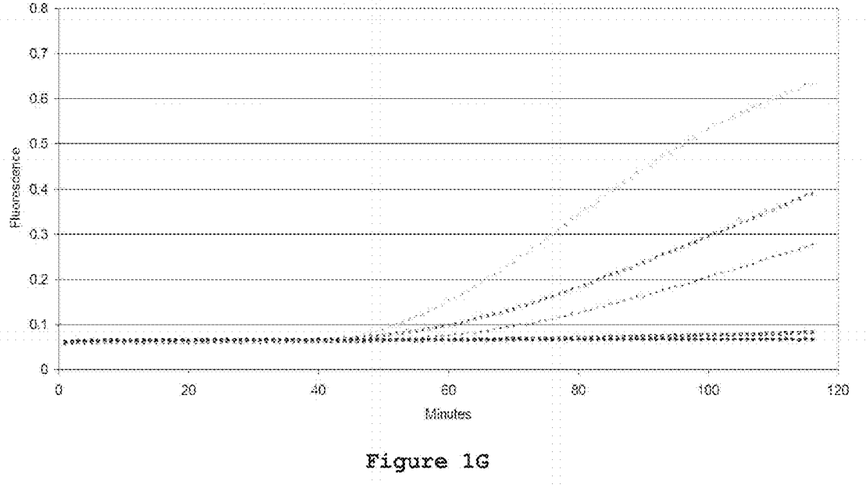
FIG. 1G: NASBA amplification HIV1 1.2 at 41° C. with T7 RNA polymerase Q3+Q744R+S767G (20 cp VIH1-B/trials; 7 technical replicates)
Figure 1H:
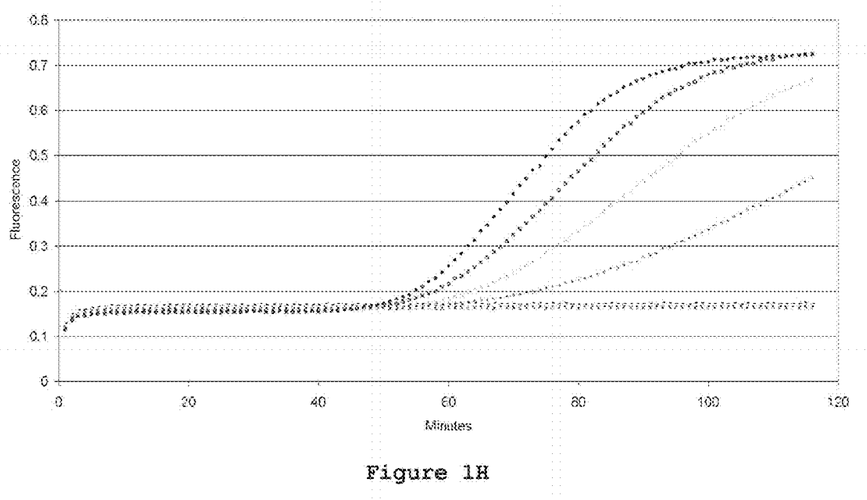
FIG. 1H: NASBA amplification HIV1 1.2 at 47° C. with T7 RNA polymerase Q3+Q744R+S767G (20 cp VIH1-B/trials; 7 technical replicates).

FIGS. 1A to 1H show isothermal amplifications at 41° C. (1A, 1C, 1E, 1G) and 47° C. (1B, 1D, 1F, 1H) carried out with the wild T7 RNA polymerase (WT) (FIGS. 1A and 1B) and various mutants 7 replicates per trials (FIGS. 1C to 1H). These fluorescent curves demonstrate the advantage of using thermostable T7 RNA polymerase mutants during a NASBA isothermal amplification at a higher temperature compared to wild T7 RNA polymerase.

Free Text of the List of Sequences

| | |
|---|---|
| SEQ ID NO: 1 | — |
| SEQ ID NO: 2 | DNA sequence coding for peptide HHHHHH (6xHis) |
| SEQ ID NO: 3 | oligonucleotide Q744R |
| SEQ ID NO: 4 | oligonucleotide Q744R anti |
| SEQ ID NO: 5 | oligonucleotide Q744L |
| SEQ ID NO: 6 | oligonucleotide Q744L anti |
| SEQ ID NO: 7 | oligonucleotide Q744P |
| SEQ ID NO: 8 | oligonucleotide Q744P anti |
| SEQ ID NO: 9 | oligonucleotide C510R |
| SEQ ID NO: 10 | oligonucleotide C510R anti |
| SEQ ID NO: 11 | oligonucleotide S767G |
| SEQ ID NO: 12 | oligonucleotide S767G anti |
| SEQ ID NO: 13 | oligonucleotide T7-Min |
| SEQ ID NO: 14 | oligonucleotide T7-plus |
| SEQ ID NO: 15 | Molecular marker MB1 FAM Dabcyl |
| SEQ ID NO: 16 | — |

The invention claimed is:

1. A T7 RNA polymerase comprising the amino acid sequence of SEQ ID NO: 16 that is mutated at position 744, wherein the glutamine (Q) at position 744 is replaced by an amino acid selected from arginine (Q744R), leucine (Q744L) or proline (Q744P).

2. The RNA polymerase of claim 1 comprising the mutation Q744R.

3. The RNA polymerase of claim 1 comprising the mutations F849I, F880Y and S430P.

4. The RNA polymerase of claim 3 comprising the mutation C510R.

5. The RNA polymerase of claim 3 comprising the mutation S767G.

6. A gene coding the T7 RNA polymerase of claim 1.

7. An expression vector comprising the gene of claim 6 and the appropriate expression sequences.

8. A cell transformed with the vector of claim 7, and capable of expressing mutated RNA polymerase.

9. A method for amplifying nucleic acids, the method comprising the step of using the RNA polymerase of claim 1 in a transcription amplification reaction of nucleic acids.

10. The method of claim 9, wherein said transcription amplification reaction of nucleic acids is an isothermal transcription amplification reaction of nucleic acids.

11. A mixture of enzymes used in an isothermal transcription amplification reaction comprising:
the RNA polymerase of claim 1; and
an enzyme having a reverse transcriptase activity.

12. The mixture of enzymes of claim 11, said enzyme having a reverse transcriptase activity also having an RNAse H activity.

* * * * *